(12) United States Patent
Smith et al.

(10) Patent No.: US 7,435,059 B2
(45) Date of Patent: Oct. 14, 2008

(54) FLOW CONTROLLED BLOOD PUMP SYSTEM

(75) Inventors: William A. Smith, Lyndhurst, OH (US); Leonard A. R. Golding, Auburn Township, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 684 days.

(21) Appl. No.: 10/378,444

(22) Filed: Mar. 3, 2003

(65) Prior Publication Data

US 2003/0139643 A1 Jul. 24, 2003

Related U.S. Application Data

(63) Continuation-in-part of application No. 08/936,317, filed on Sep. 24, 1997, now abandoned.

(51) Int. Cl.
*F04B 49/00* (2006.01)

(52) U.S. Cl. .................. 417/26; 417/44.11; 417/295

(58) Field of Classification Search .............. 417/26, 417/295, 300, 44.11
See application file for complete search history.

(56) References Cited

U.S. PATENT DOCUMENTS

| | | | | |
|---|---|---|---|---|
| 3,289,918 | A | * | 12/1966 | Adams ................. 417/228 |
| 4,135,253 | A | | 1/1979 | Reich et al. |
| 4,212,599 | A | * | 7/1980 | Lantermann ............ 417/295 |
| 4,247,263 | A | * | 1/1981 | Pech et al. .............. 417/295 |
| 4,589,822 | A | | 5/1986 | Clausen et al. |
| 4,643,641 | A | | 2/1987 | Clausen et al. |
| 5,017,103 | A | | 5/1991 | Dahl |
| 5,049,134 | A | | 9/1991 | Golding et al. |
| 5,098,256 | A | | 3/1992 | Smith |
| 5,100,374 | A | | 3/1992 | Kageyama |
| 5,118,264 | A | | 6/1992 | Smith |
| 5,145,333 | A | | 9/1992 | Smith |
| 5,147,187 | A | | 9/1992 | Ito et al. |
| 5,242,268 | A | | 9/1993 | Fukazawa et al. |
| 5,307,288 | A | * | 4/1994 | Haines ................. 415/144 |
| 5,348,444 | A | | 9/1994 | Metzinger et al. |
| 5,370,509 | A | | 12/1994 | Golding et al. |
| 5,399,074 | A | | 3/1995 | Nose et al. |
| 5,447,414 | A | * | 9/1995 | Nordby et al. ......... 417/44.11 |

OTHER PUBLICATIONS

Golding, Leonard A.R., et al. "The Cleveland Clinic Rotodynamic Pump Program," *Artificial Organs*, 20(6): 481-484, Blackwell Science, Inc, Boston (Jan. 1996).

(Continued)

*Primary Examiner*—Charles G Freay
(74) *Attorney, Agent, or Firm*—Fay Sharpe LLP

(57) ABSTRACT

A system for pumping blood to assist or assume the cardiac function of a patient is characterized by a blood pump that exhibits a steep performance curve such that only small changes in pump flow occur for large changes in differential pressure across the pump. The pump therefore exhibits flow-limiting characteristics to protect the physiological system against harmful flow rates or pressures. Pump flow may also be limited by controlling the current provided to a driver from a power supply or by suitable restrictions within or external to the pump housing.

14 Claims, 8 Drawing Sheets

OTHER PUBLICATIONS

Tanaka, Shinobu, et al., "A Compact Centrifugal Blood Pump for Extracorporeal Circulation: Design and Performance," *Journal of Biomechanical Engineering*, Aug. 1987, vol. 109 pp. 272-278.

Nishimura, Kazunobu, et al. "Control of the Pressure Flow Relationship with a Magnetically Suspended Centrifugal Pump in a Chronic Animal Experiment (Pressure Flow Relationship of MSCP)," *ASAIO Journal*, vol. 43, M553-M446, 1997.

* cited by examiner

FLOW CONTROLLED BLOOD PUMP SYSTEM

BACKGROUND OF THE INVENTION

This application is a continuation-in-part application of application U.S. Ser. No. 08/936,317, filed Sep. 24, 1997 now abandoned.

The present invention relates to the art of pumping devices and cardiac prosthesis. More particularly, the present invention relates to motor-driven rotodynamic pumps for use as blood pumps in the human body and to control systems and techniques for such blood pumps.

There has been much effort recently in the medical community to develop artificial devices and systems that are capable of assisting or completely assuming the cardiac function in patients having limited cardiac function or who have undergone removal of a diseased natural heart. Some of this effort has focused on duplicating the pulsatile mechanical action of the natural human heart. On the other hand, it has been recognized that human life may be sustained with non-pulsatile blood flow in the circulatory system. Accordingly, recent research has included the evaluation of non-pulsatile pumping devices, which provide a continuous flow of blood to the circulatory system, as prosthetic devices for assuming or assisting cardiac function. Typically, these non-pulsatile pumps take the form of rotodynamic blood pumps, also known as continuous flow blood pumps, centrifugal blood pumps, mixed flow blood pumps, or axial flow blood pumps. Rotodynamic pumps offer the advantage of reduced size and weight, simpler design, increased dependability and low cost compared to positive displacement or pulsatile pumping devices used as implantable pumps.

In the human body, the peripheral vascular resistance and venous "tone" are controlled by the body according to the needs of the body's organs. Blood vessels constrict (vasoconstriction) and expand (vasodilation) in response to neural impulses associated with blood demand required by the body's organs. This action results in pressure and flow variations within the circulatory system. In a sense, the natural heart is the servant of the circulatory system and the amount of blood pumped is dependent on the requirements of the body. That is, the cardiac output (the volume of blood delivered by the heart within a given time period) is equal to the venous return (the volume of blood returning to the heart within that same time period). The human heart is characterized by intrinsic control that responds to changes in demand for blood flow by the circulatory system. Illustrative of this characteristic is the fact that extrinsic control implements are not necessary when a human heart is transplanted and no direct neural connection is required for the transplanted heart to assume the cardiac function in the host body.

Rotodynamic pumps typically operate or are controlled to maintain a defined pressure difference between the pump inlet and outlet. Usually, pump controllers do this by maintaining a set impeller speed. The performance characteristics of a pump are often expressed by a performance curve which depicts the relationship between the pressure differential across the pump and the pump flow for a given pump operating speed.

The use of rotodynamic blood pumps as cardiac prosthesis presents unique problems with regard to the interaction between the pump and the human circulatory system. Compared to the natural heart and some artificial hearts, conventional rotodynamic pumps are not as apt to respond correctly to changes in pressure and flow induced by the human circulatory system. This is due in part to the fact that, unlike the natural human heart, rotodynamic pumps have no inherent sensitivity to inlet pressure (preload) or outlet pressure (afterload). When pump speed is maintained at a controlled value, pump flow does not change appreciably unless there is a change in the pressure difference between the inlet and outlet—the pressure differential across the pump. Thus, in the case of a pump being used as a blood pump, a change in the inlet pressure, i.e., the venous return path of the circulatory system, which is accompanied by a like change in the outlet pressure, i.e., the pressure at the pump outlet, may occur without any significant change in the pump flow since the pressure differential across the pump remains constant. This contrasts sharply with the operation of the natural heart, in which a significant increase in flow is usually associated with an increase in venous pressure, with only a small and frequently transient effect from systemic pressure. Whether a change in pressure difference is caused by an increment in the inlet pressure or the outlet pressure is not particularly critical to the rotodynamic pump. However, with regard to the physiological system, a five or ten mm-Hg preload pressure change has a different physiologic significance than an equal amount of afterload change. As a consequence, if the outlet pressure falls to a low level, an inappropriately designed and/or controlled rotodynamic pump may urge flow through the system until the inlet pressure falls to a correspondingly low and perhaps dangerous level, where upstream vascular structures may collapse from lack of blood pressure. Conversely, if the outlet pressure becomes high, the inlet pressure might rise a similar amount, and, in extreme cases, the direction of flow might even reverse. The change, which is compensatory from the pump's point of view, is potentially maladaptive relative to the needs of the physiologic system being supported. In conventional pump constructions, the degree of maladaptivity of the pump is an inherent result, in part, of the nature of the performance curve associated with known pump designs. This problem may be exacerbated if the natural heart retains some contractile function, causing the artificial pump pressure difference to oscillate between very low levels during natural heart systole, and high levels during diastole. Within one heartbeat the system may experience excessive forward pumping, and reversed flow.

In clinical practice today, rotodynamic pumps are controlled by external consoles, and an operator increases or decreases speed according to medical judgement. Furthermore, most clinical cases to date with rotodynamic pumps have been done with external pumps which require long inflow and outflow cannulae. These cannulae contribute a relatively large pressure drop between the pump and the physiological system, making physiologic pressure swings a smaller part of the total resistance value resulting from the cannulae and physiological system combined. It has been proposed to use a system of pressure or flow transducers, in cooperation with the pump and a control algorithm, to produce a closed loop feedback controlled system for pump flow. However, such techniques or devices are often complex and offer no economically feasible solution to the problems of providing low cost and dependable blood pumping systems. It has also been proposed to control these rotary pumps by measuring the motor electrical current, and making speed adjustments based on assumptions regarding the relationship between flow, current, and speed. These protocols require additional logic and fallback positions for instances where the assumed relationships are not valid.

It would, therefore, be desirable to provide a blood pumping system that alleviates the aforementioned problems such that external sensors and control implements are not necessary for the pump to maintain an acceptable output and preserve the integrity of the circulatory system over long periods of time, a wide level of variation in residual ventricular activity, and a broad range of patient activity levels.

BRIEF SUMMARY OF THE INVENTION

In accordance with the present invention, there is provided a rotodynamic blood pumping system that addresses the aforementioned problems in the prior art. The pump comprises a housing equipped with inlet and outlet fluid passages in communication with a pumping chamber. An impeller is received within the chamber for propelling the fluid from the inlet to the outlet. The impeller is coupled to a motor or other prime mover. The amount of fluid flow moved from pump inlet to pump outlet is proportional to the pressure differential maintained across the ports by the system being supported by the pump. According to the present invention, the pumping system is configured to provide a pressure/flow performance curve in the vicinity of the operating set point such that a change in flow is relatively small compared to the change in pressure; that is, the constant of proportionality $\Delta Q/\Delta P$ is small. For a fifty percent (50%) change in the baseline pressure differential, the change in flow might be on the order of twenty percent (20%). The pump configuration is such that flow through the pump is limited in the presence of small pressure differentials across the pump, thereby preventing excess flow which might damage the physiologic system. Similarly, in the face of large pressure differentials, the pressure producing capability of the pump is adequate to maintain life sustaining flows.

According to another aspect of the invention, the outlet fluid passage includes a flow restrictor, so configured as to contribute to the appropriate slope of the pressure/flow curve of the pumping system.

In accordance with another aspect of the invention, the resistance of the outflow conduit connecting the pump to the physiologic system is configured to partially insulate the pump outlet from the effects of pressure changes in the receiving end of the physiologic system. This results in the flow output of the pump system remaining closer to the mean set point over the full range of circulatory pressures.

According to yet another aspect of the invention the motor and its energy supply are controlled so that a decrease in load represented by falling flow results in an increase in the rotational speed of the impeller. This increases the pressure capability of the pump, improving its ability to deliver and control flow. An increase in flow has an exactly opposite effect.

According to yet another aspect of the invention, a switch permits the set point for the flow to be selected to suit the needs of different patients, or one patient during different phases of recovery.

A major benefit of the invention is the ability of the pumping system to maintain flow in a narrow range, safe and satisfactory for the served system, without the use of external sensors and control loops. Another benefit is the potential to shift the mean set point of flow by simple and reliable means. Other benefits and advantages for the subject invention will become apparent to those skilled in the art upon a reading and understanding of the specification.

BRIEF DESCRIPTION OF THE DRAWINGS

The invention may take physical form in certain parts and arrangements of parts, the preferred embodiments of which will be described in detail in the specification and illustrated in accompanying drawings which form a part hereof and wherein.

DETAILED DESCRIPTION

Figure 1:
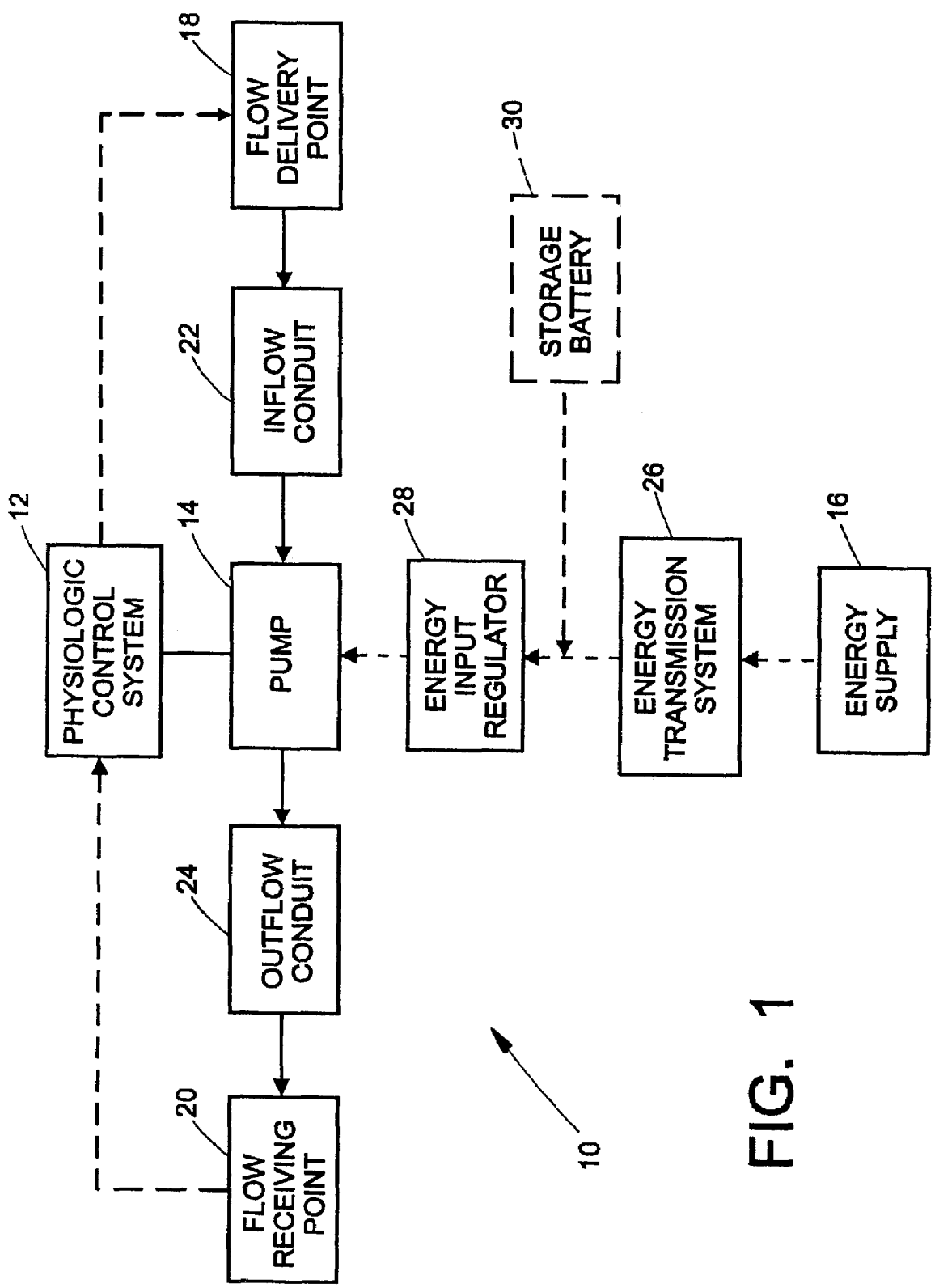
FIG. 1 is a block diagram of a pumping system according to the present invention.

Referring now to the drawings wherein the showings are for purposes of illustrating the preferred embodiments of the invention only and not for purposes of limiting same, FIG. 1 shows block diagram of a blood pumping system according to the present invention. The human physiologic system is represented by block 12 and interfaces with pump 14 via flow receiving point 20 and flow delivery point 18. Typically, in a blood pump application, flow delivery point 18 may be a cannulation of the atrium or ventricle of the natural heart. Inflow conduit 22 may be a fluid carrying duct connecting the cannulation point to the inlet port of the pump. Outflow conduit 24 is another fluid carrying duct that connects pump outlet port to the flow receiving point 20. With a blood pump system, this point would usually be an anastomosis to a major artery.

The function of the biological control system 12 is well-known and a detailed discussion thereof is not necessary for an understanding of the present invention. It is sufficient to note that the biological control system 12 results in pressure and flow variations at the inlet and outlet of the pump which may occur independently of one another. Energy input regulator 28 is a means to control the energy input to the prime mover of the pump, so as to facilitate control of pump 14. The prime mover is preferably an electric motor, and the regulator controls the voltage, frequency, or current of electricity supplied to the motor. However, it will be appreciated that other types of prime movers, such as hydraulic or pneumatic motors, or thermal systems, which have parameters analogous to electric voltage, frequency, and current, could be adapted as prime movers of this system.

Energy transmission system 26 serves to conduct the power to energy input regulator 28 from the principal energy supply 16. Energy transmission system 26 may be a simple cable or conduit, or an electrical transformer-like transcutaneous transmission system. Storage battery 30, permits continuous power to energy input regulator 28 during transient interruption of the energy transmission system, and may include recharging provisions. Energy transmission system 26, principal energy supply 16 and battery 30 may comprise implements that are well-known in the art and a detailed discussion thereof is not necessary for an understanding of the present invention.

Figure 2:
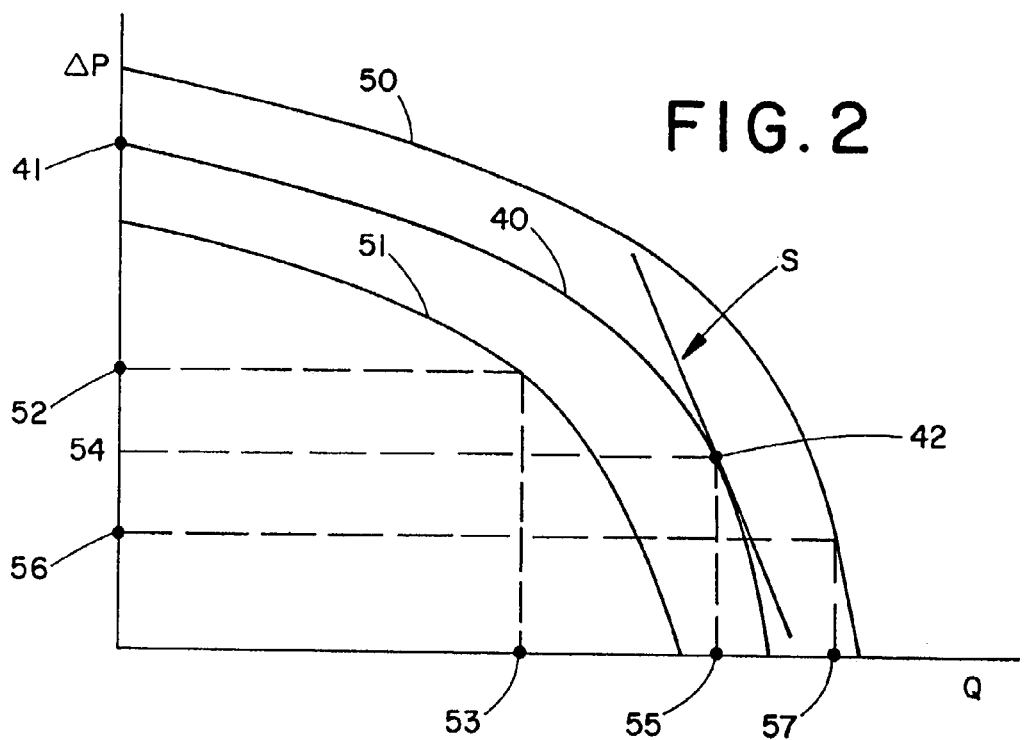
FIG. 2 is a graphical representation of three flow versus pressure differential curves for a pumping system according to the present invention.

The desired performance of the pump system according to the present invention can be understood from a study of FIG. 2, which depicts performance curves corresponding to three pump operating speeds. Curve 40 represents a nominal operating speed performance curve at which the pumping system is characterized by a maximum output pressure rise or "shut off" pressure 41 corresponding to a zero flow condition. As flow increases, the pressure differential across the pump or pumping system decreases. In accordance with the present invention, the pumping system is configured to provide a performance curve which increases in steepness as flow increases, with a very steep slope S through the nominal operating point 42. Preferably, this slope—the change in flow rate divided by the change in pressure differential—is on the order of about −3% or less (liters-per-minute/mm-Hg) such that, at the nominal operating set point of the pump, a change in pressure of about 50 mm-Hg between the pump inlet and outlet produces a change in flow of no more than 1 liter-per-minute. If the physiologic system should so operate to decrease the pressure differential across the pumping system, the configuration of the pumping system limits the ability of the pumping system to pass additional flow, hence preventing a significant increase in flow despite the change in applied pressure differential. In the case of an increased applied pressure, as flow drops, an opposite change in impeller characteristics would compensate for the effect of the external pressure, again holding the flow change within a limited band.

Also shown banding the nominal rotational speed 40 are maximum operating speed performance curve 50 and minimum operating speed performance curve 51. A maximum expected imposed pressure rise 52, extrapolated to the low tolerance speed curve 51, yields a minimum flow 53. Similarly, the nominal pressure 54 and nominal rpm 40 yield a nominal flow 55. Minimum pressure 56 and maximum rpm 50 cooperate to produce maximum flow 57.

In accordance with the present invention, the pumping system is configured such that the flow excursions around the nominal operating point 42 are never so high, or low, as to cause damage to the system. The slope of the performance curve therefore operates to reduce the flow increase or decrease associated with a given change in the pressure differential across the pumping system. The absolute values of these flows will be application dependent. In the case of a blood pump application, the acceptable nominal and limit flows would depend on the size, sex, and age of the patient and what, if any, flow was still produced by the damaged natural heart. As an example, in a given human, a natural heart limited to an output of 2.5 liters/minute would result in severe impairment, and a poor quality of life. A ventricle assist device providing 4 liters/minute additional flow would result in a normal resting cardiac output. If the applied pressure rose, and assist device flow fell to 3 liters/minute, life would be maintained until treatment could be obtained, even if the natural heart fails completely; with some residual ventricular function, the patient could be quite comfortable with the summed flows. If pressure fell, and the pump flow increased to 5 liters/minute, the patient would not be seriously over pumped. If available filling flow had not increased, the assist device might divert some flow that otherwise would have gone through the natural aortic valve, but the blood in any case would reach the systemic circulation.

Figure 3:
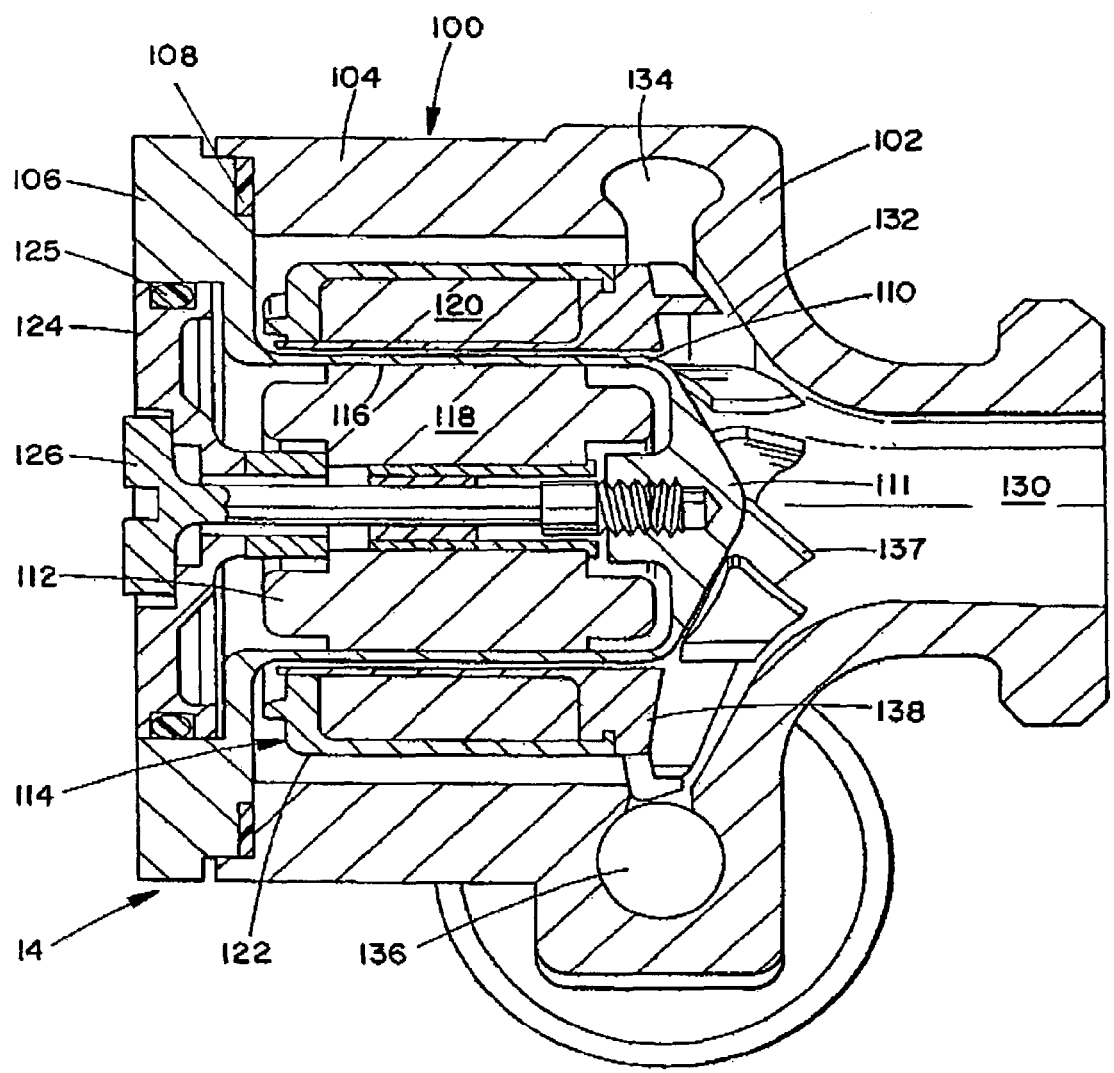
FIG. 3 is a cross-section of a pump according to the present invention.

A pump 14 that is suitable for achieving the desired performance characteristics is illustrated in cross-section in FIG. 3. Pump 14 includes a housing 100 which comprises two portions, impeller housing portion 102 and motor housing portion 104. A housing cover 106 is also provided. Housing 100 may be constructed from any biocompatible material, such as titanium. Housing cover 106 is secured to housing 100 using conventional fasteners (not shown) and a resilient seal 108 is provided therebetween. Housing cover 106 includes a generally hollow cylindrical axial extension 110 which houses stator 116 of motor 112 and includes a conical tip 111. Stator 116 includes a ferrous stack 118 and suitable conductors (not shown) for carrying current thereto. Stator 116 is secured within axial extension 110 by a threaded fastener 126 which also secures motor cover 124 in sealing engagement with housing 100 via O-ring 125. Motor 112 also includes an annular rotor 114 which is concentric with axial extension 110 and includes permanent magnet 120 therein. Rotor 114 constitutes a driver 122 for impeller 137 and is secured to the base 138 of impeller 137.

Figure 4A:
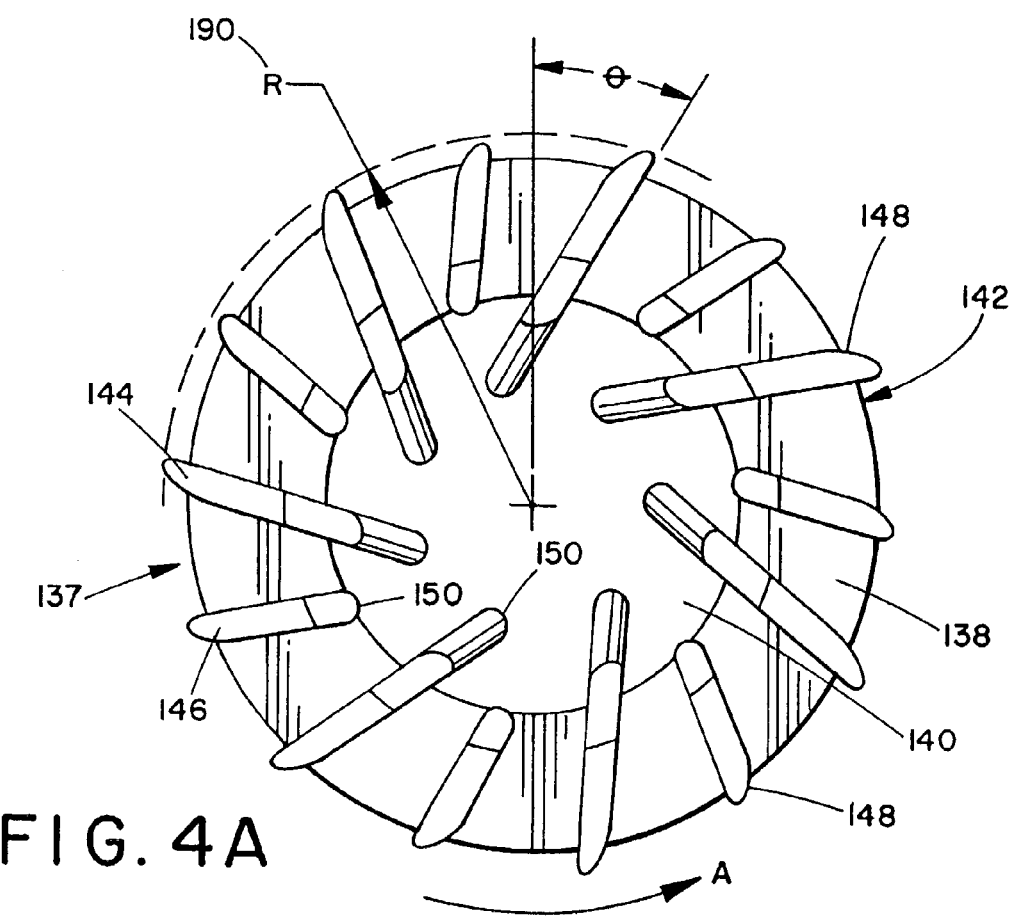
FIGS. 4A-4C illustrate an impeller design that is suitable for accomplishing the present invention.
Figure 4B:
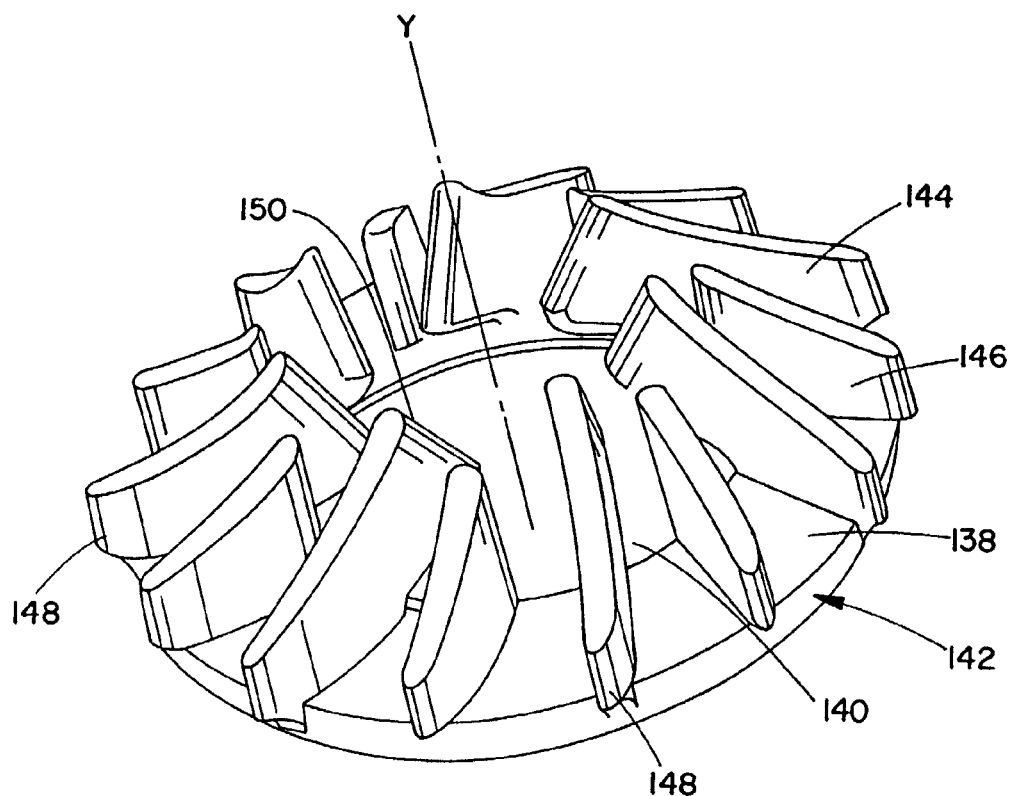
Figure 4C:
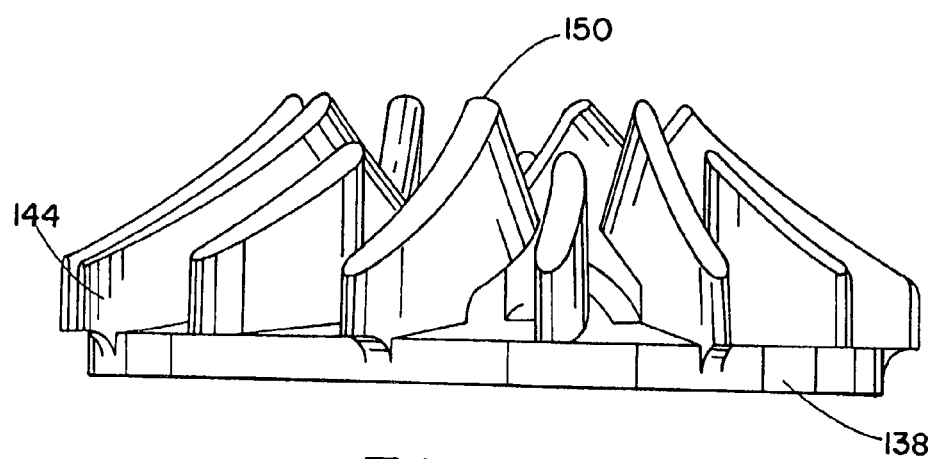

Impeller housing portion 102 of housing 100 defines inlet 130 which communicates with impeller chamber 132 and annular chamber 134 situated around the outer periphery of impeller 137. Pump outlet 136 is a generally cylindrical passage which communicates with annular chamber 134. Impeller 137, which will be described below in more detail with reference to FIGS. 4A-4C, is configured to fit around conical tip 111 of axial extension 110. Impeller chamber 132 of housing 100 is shaped complementarily to the blades of impeller 137 to define flow passages from inlet 130 to annular chamber 134. In operation, rotation of impeller 137 imparts centrifugal force to the blood, thereby conveying it from inlet 130 outward into annular chamber 134 and pump outlet 136.

Referring to FIGS. 4A-4C impeller 137 comprises an annular base 138 which includes a circular recess 140 and impeller base perimeter 142. Extending from base 138 and fixed thereto are main impeller blades 144 and splitter blades 146, which extend between main blades 144 in alternating fashion. Splitter blades 146 give more guidance to the flow at the outer diameter of the impeller where the spacing between main blades 144 is relatively large, and also reduce the net flow area. As a result, the flow angle of blood better follows the blade angle, enhancing pump performance. Referring to FIG. 4A, which is a front view of impeller 137, it can be seen that the impeller main blades 144 and splitter blades 146 are flat, with no curvature, and are provided with a tapered or curved outer edge 148. Tapered or curved outer edge 148 provides smooth velocity transitions and prevents separated blade wakes as impeller 137 rotates in the direction of arrow A. It will be appreciated, however, that curved blade designs may be suitable for some applications of the invention, provided that the desired performance characteristics of the pumping system as exemplified in FIG. 2 are achieved.

Main blades 144 and splitter blades 146 also include rounded inner edges 150 to preserve the integrity of the blood. Main blades 144 and splitter blades 146 are disposed at an angle THETA to the diameter of the base 138. Applicants have found that suitable results are obtained if THETA is between 35 and 75 degrees. As shown in FIG. 4B, the inner edges 150 of main blades 126 are angled with respect to the axis of the impeller. These angled edges 150 permit impeller 137 to accommodate conical tip 111 (FIG. 3) of axial extension 110. While the present embodiment has been described as a radial flow pump, it will be appreciated by anyone with reasonable skill in the art that similar performance goals could be met with mixed flow or axial flow pump configurations.

In some cases it may not be necessary, or desirable to produce the flow-limiting performance characteristic solely by selection of the dimensions and proportions of the impeller and pump flow paths. The desired effects of the present invention may also be produced or enhanced by providing fluid resistances in other parts of the pumping system.

Figure 5:
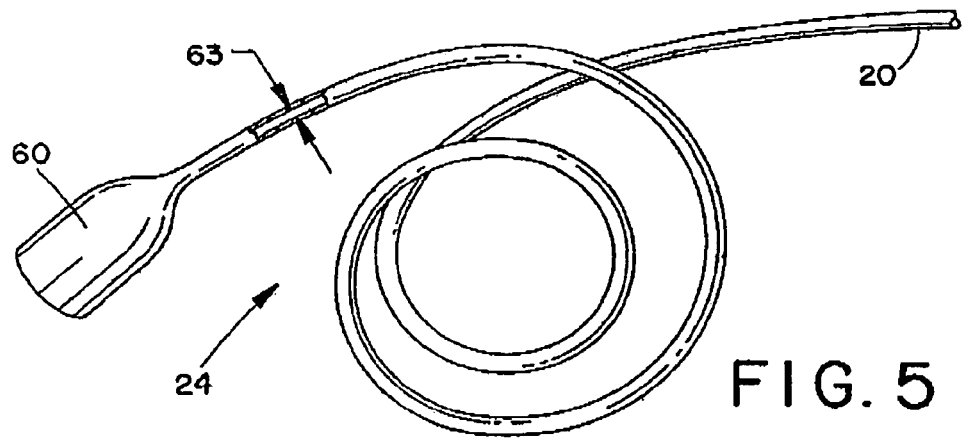
FIG. 5 is a view of an outflow conduit suitable for use in a pump system according to the present invention.

FIG. 5 illustrates flow restrictor in the form of an outflow conduit 24 which is suitable for use in a pumping system according to the present invention. Conduit 24 is provided with a pump connection end 60 and a flow receiving point end 61. The internal diameter 63 of the conduit is selected to be small, yet large enough to prevent flow velocities or patterns that may damage the blood. The length from inlet 60 to outlet 61 is selected such that, in combination with diameter 63, a specific resistance to flow can be obtained.

Figure 6:
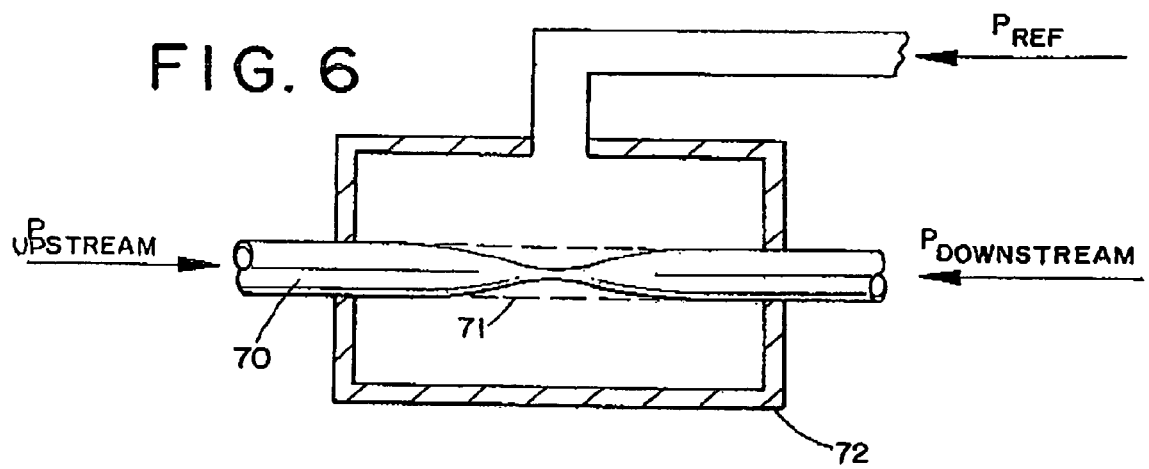
FIG. 6 is a cross-section of a Starling resistor suitable for use in a pump system according to the present invention.
Figure 7:
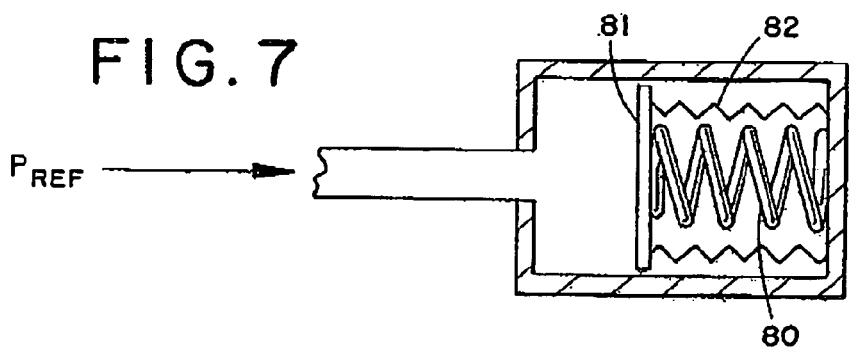
FIG. 7 is a cross-section of a constant pressure reservoir suitable for use in a pumping system according to the present invention.

An alternate approach to obtaining a useful resistance value is schematically shown in FIG. 6. This approach incorporates a device known as a Starling resistor. Flow enters tube 70 having a flaccid section 71. The flaccid section is surrounded by a case 72, which houses a fluid subjected to reference pressure $P_{ref}$. Pressure $P_{upstream}$ is essentially the pressure at the pump outlet port. It is known that for this arrangement, the back pressure resisting flow in tube 70 will be the reference pressure $P_{ref}$ unless or until the downstream pressure exceeds the reference pressure. The downstream pressure $P_{downstream}$ will be equal to the reference pressure $P_{ref}$ subtracted from the upstream pressure $P_{upstream}$. The combination of a Starling resistor with an appropriate reference pressure $P_{ref}$ may be used to provide or enhance the flow-limiting characteristics of the pumping system as described above. FIG. 7 illustrates a spring-loaded pressure reservoir suitable for providing the reference pressure $P_{ref}$ for the Starling resistor described above. The device comprises a spring 80 and bellows 82 which are secured to a piston 81. Reference pressure $P_{ref}$ will be equal to the force provided by spring 80 divided by the area of piston 81.

In general, it is undesirable to throttle the pump inlet because throttling can produce excessively lowered pressures and possibly cavitation. However, a Starling resistor such as that illustrated in FIG. 6 can be used on the pump inflow conduit 22 (FIG. 1) to prevent overpumping. In this case, the pressure $P_{upstream}$ would be the filling pressure upstream of the flow delivery point 18 (FIG. 1). Pressure $P_{downstream}$ would essentially be the pump inlet pressure. The reference pressure $P_{ref}$ would be selected to represent some safe minimum pressure level for pressure $P_{upstream}$, perhaps −5.0 mmHg. If the pumping action resulted in the pressure $P_{upstream}$ falling below pressure $P_{ref}$, the Starling resistor would collapse and flow would cease until pressure $P_{upstream}$ rose above pressure $P_{ref}$. As a result the tissue around and before the flow delivery point 18 would be protected from the effect of low pressure and the inflow conduit 22 would not be permanently blocked by the forced ingress of a tissue plug. The effect of a Starling resistor in this application is usefully simulated by using a body cavity pressure, such as intrathoracic pressure, as pressure $P_{ref}$ and replacing the flaccid section 71 with one of some stiffness, so that the resistance to deformation would approximate that of a pressurized, near zero stiffness tube section.

Figure 8:
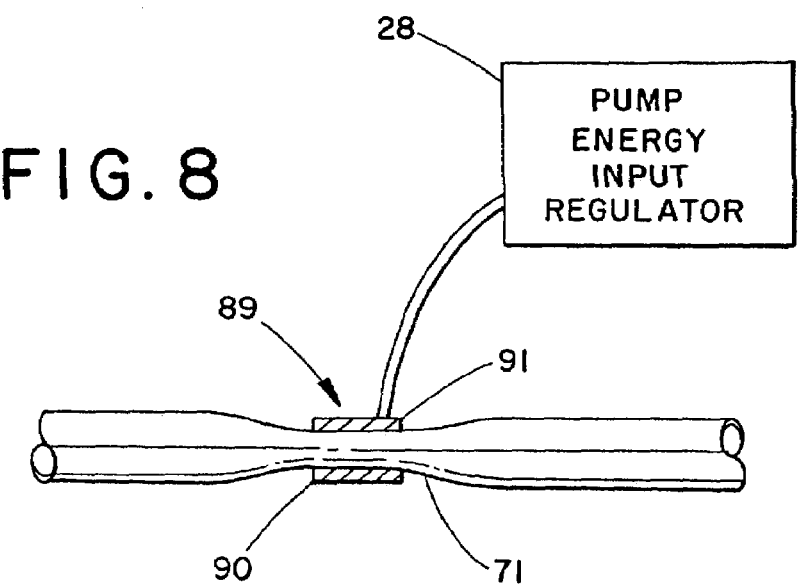
FIG. 8 is a cross-section of a deformable tube with a proximity switch suitable for use in a pumping system according to the present invention.

Alternatively, an over-pumping or under-pumping condition may be sensed according to the present invention by incorporating a deforming cross-section in the inflow or outflow conduit. As shown in FIG. 8, a proximity switch 89, such as a magnetically operated reed switch, could be situated on the flaccid tube section 71 and used to sense under-pumping or over-pumping. Magnet 90 acts on the contact of switch 91. If the "flaccid" section 71 collapses or is expanded beyond predetermined limits, the switch 89 produces a signal to pump energy input regulator 28 which may be programmed or otherwise configured to alter the pump speed as appropriate. The electronics in pump energy input regulator 28 may include a time delay, or a positional hysteresis in the switch opening and closing, to ensure stability of operation by preventing hair-triggering between pump speed control values.

Figure 9:
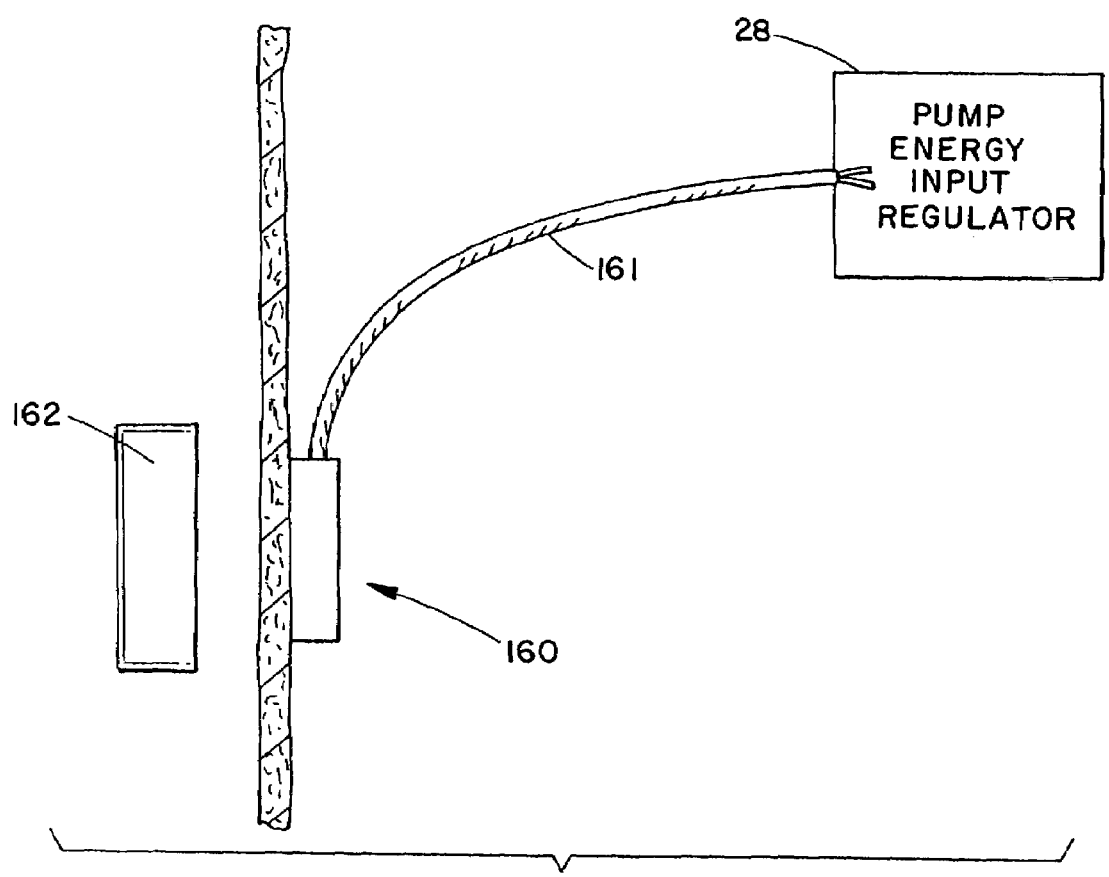
FIG. 9 is an illustration of a subcutaneous, remotely triggered set point changing switch suitable for use in a pumping system according to the present invention.

A further modification to control technique for the energy input regulator 28 is illustrated in FIG. 9. It is in the form of a subcutaneous switch 160, such as a magnetically triggered reed switch, which permits the operator to modify the control characteristics of the pump from one rpm, current, or flow control algorithm to another. As shown in FIG. 9, switch 160 is connected to the pump energy input regulator 28 by wires 161. The switch 160 is located subcutaneously in a patient and independent of other system components. Magnet 162 is brought into the vicinity of switch 160 by the patient or doctor to select between predetermined control configurations.

As an alternative technique for controlling the pump flow according to the present invention, flow may be limited to an acceptable range by algorithmic control of the power of the pump motor. It is known that the flow and the power corresponding to a given pump speed have a quantifiable relationship. By regulating the energy input to the pump motor according to a desired specific value, a more nearly constant pump flow may be obtained. If the inlet to outlet pressure difference falls, the tendency of the impeller in an uncontrolled pump would be to increase flow, resulting in an accompanying increased current demand by the motor. However, with power limited, the motor will slow or will operated within a predefined flow range. This will decrease the pump pressure capability and maintain pump flow within acceptable limits.

Motor power may be controlled according to an algorithm that relies on the known relationships between pump flow and power in rotodynamic pump operation. The following relationships are known from pump theory:

$$\phi = \text{Flow Coefficient} = \frac{C_1 Q}{N R^3} \quad (1)$$

$$\pi = \text{Power Coefficient} = \frac{C_2 P_S}{\rho N^3 R^5} \quad (2)$$

$$\phi = \text{Monotonic Function of } \pi = f(\pi) \quad (3)$$

$$Q = f\left(\frac{C_2 P_S}{\rho N^3 R^5}, \frac{N R^3}{C_1}\right) \quad (4)$$

where $C_1$ and $C_2$ are constants that depend on only the dimensional units used, N is equal to the pump speed expressed as revolutions per minute (r.p.m.); R is the radius of the pump 190; Ps is the shaft power; rho is fluid density; and Q is the flow rate.

The speed (rpm) and power of the motor are readily measured within the energy regulator-motor system by well known means. Therefore, by calibration of the system to determine the constants C1 and C2 and therefore the functional relationship between flow, rpm, and power, it is possible to control pump speed and power to hold a nearly constant flow, without ever measuring flow or pressure directly.

Figure 10:
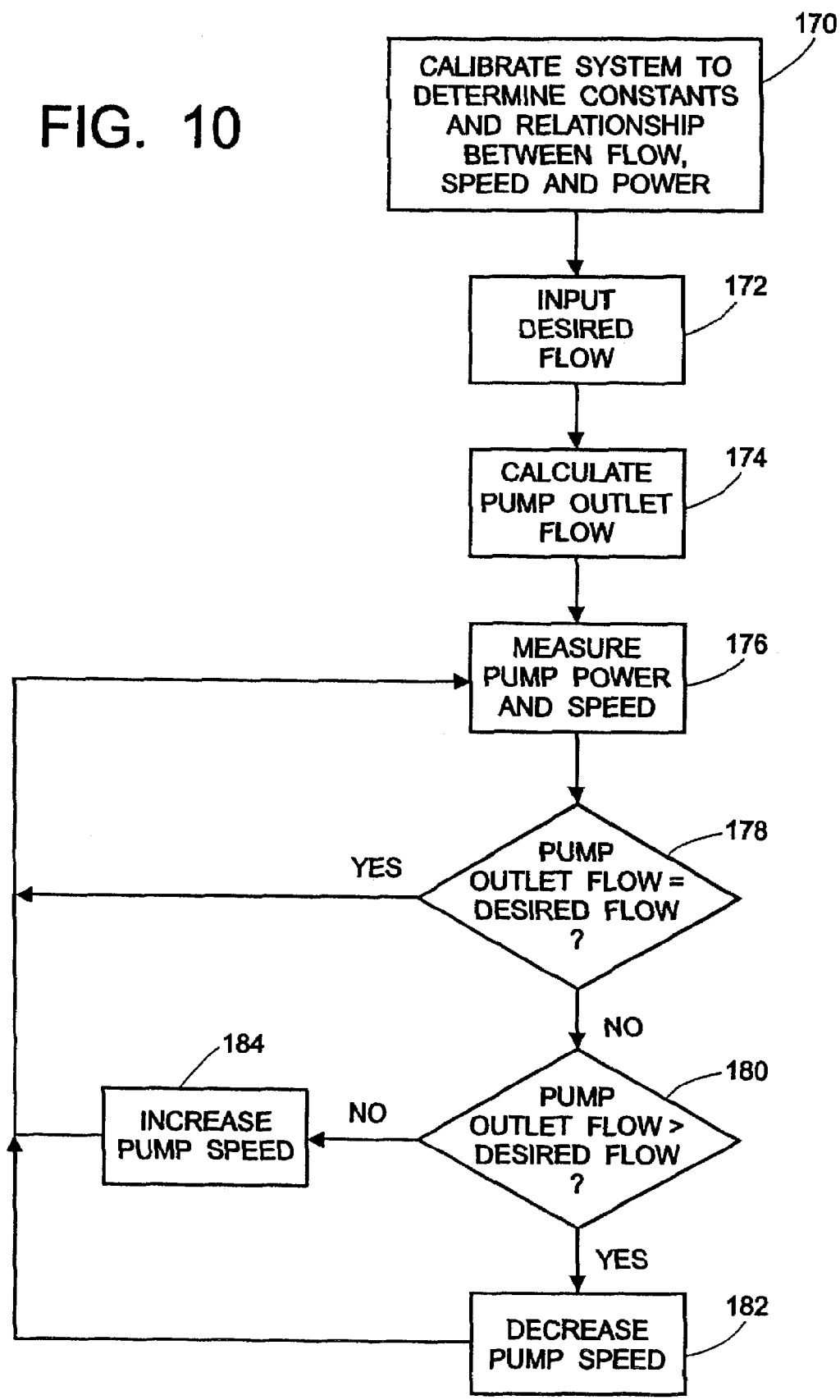
FIG. 10 is a flow chart of a control algorithm for controlling the pump motor current of a pumping system according to the present invention.

FIG. 10 is a flow chart for a control algorithm suitable for accomplishing pump control according to the present invention. At 170, the system is calibrated to determine the relationship between flow, speed and power. This may be accomplished by measuring these three parameters to determine the value of constants C1 and C2 in equations (1)-(4) above. Once determined, these constant values are stored for use in by the algorithm.

At 172, the desired pump flow is input. At 174, pump power and speed are determined and used to determine a calculated value of pump outlet flow at 176. At 178, this value is compared to the desired pump flow value. If the pump outlet flow is equal to or within a predetermined tolerance of the desired flow, the algorithm returns to 174 where new measurements are made of pump power and speed. If Qoutput is not within a predetermined tolerance of Qdesired, the algorithm branches to 180 to determine whether the pump speed should be increased (184) or decreased (182). After the appropriate adjustment to motor speed is made, the algorithm returns to 174 to again measure pump power and speed.

Figure 11:
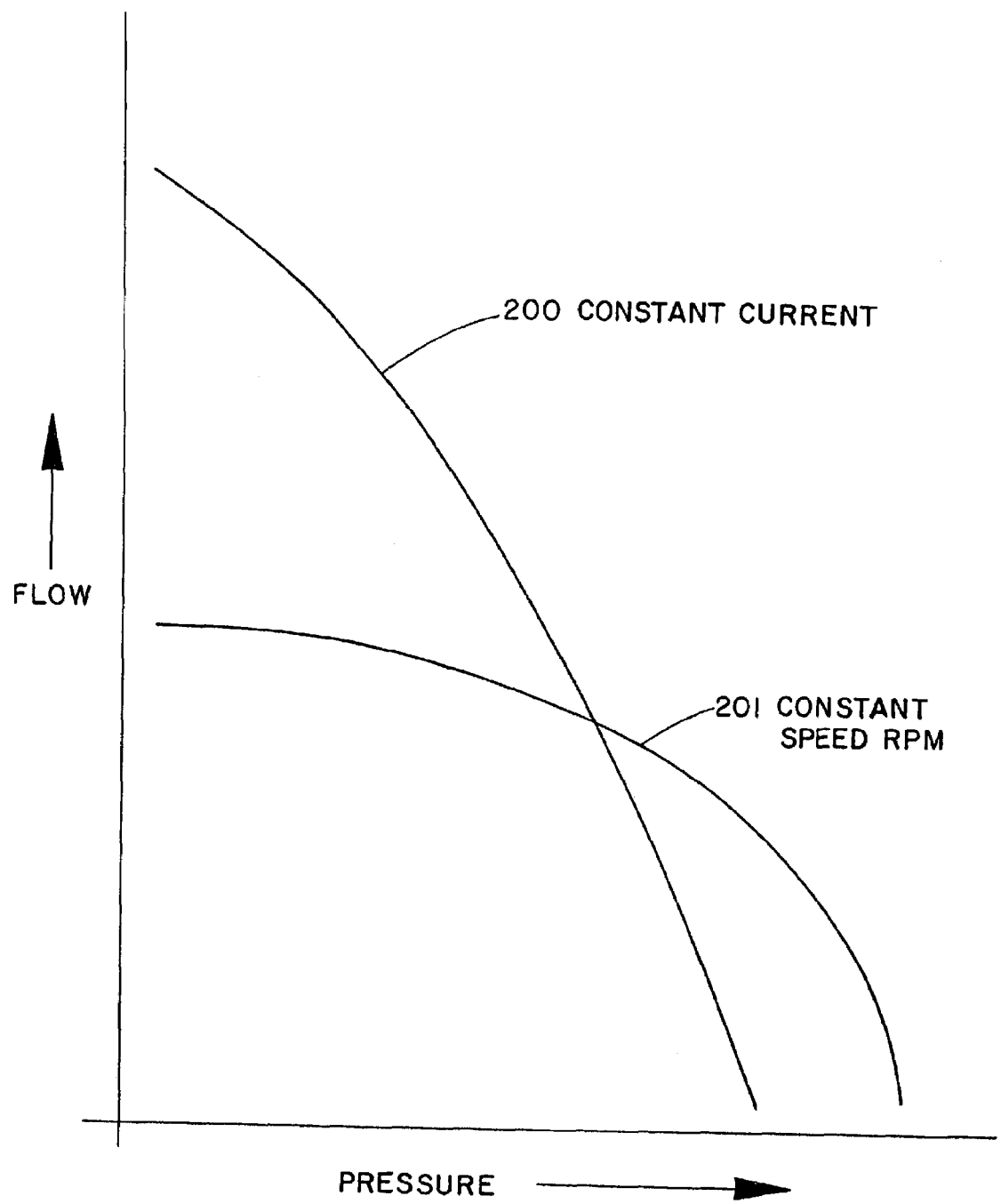
FIG. 11 is a graphical representation of two curves comparing flow versus pressure differential curves for a pumping system according to the present invention, one pumping system having a constant current and another pumping system having a constant speed RPM.

Alternatively, referring to FIG. 11, motor current, rather than power, can be controlled, resulting in flow/pressure pressure relationship at constant current 200, as compared to the flow/pressure relationship at constant speed 201, for the same or a similar impeller. In yet another alternative realization of the energy input control algorithm, the ratio of motor current to motor rotational speed can be the controlled parameter. This current to speed ratio can be calculated using linear values of the specified parameters, or in the form $I^a/rpm^b$, where a and b are power that improve the quality of the current and rotational speed relationship for a particular system.

From the foregoing, it will be recognized that flow-limiting characteristics in accordance with the present invention may be achieved by appropriate modifications to the pump geometry itself, by implements such as flow restrictors or controllers added to the pumping system external of the pump, or by a combination of the two. Moreover, flow-limiting characteristics may be incorporated into the control system for the pump. The invention has been described with reference to the preferred embodiments. Obviously, modifications and alterations will occur to others upon the reading and understanding of the specification. It is our intention to include all such modifications and alterations insofar as they come within the scope of the appended claims.

What is claimed is:

1. A system for pumping blood comprising:
   a) a rotodynamic pump including:
      i) a housing defining a chamber and an inlet and outlet in fluid communication with the chamber; and
      ii) an impeller disposed within the chamber for urging fluid from the inlet toward the outlet;
      iii) the pump having a performance curve at a nominal operating speed of the pump, the performance curve relating changes in the pressure differential across the pump to changes in flow through the pump;
   b) a driver for imparting rotational motion to the impeller;
   c) a power supply for supplying power to the driver;
   d) a regulator for regulating the power supplied from the power supply to the driver;
   e) flow limiting characteristics that maintain the flow through the pump within predefined limits throughout a wide range of pressure differentials across the pump, wherein the pump further comprises an axial extension connected to the housing having a conical tip and wherein the impeller comprises a plurality of blades configured to accommodate the conical tip.

2. The pumping system according to claim 1, wherein the performance curve is linear through a nominal operating set point of the pump.

3. The pumping system according to claim 1, wherein the direction of flow through the impeller blades is at an acute angle with respect to the axis of rotation of the impeller.

4. The pumping system according to claim 1, wherein the performance curve of the pump exhibits a change in flow of no more than 1 liter-per-minute for a change in pressure of 50 mm-Hg between the pump inlet and pump outlet.

5. The pumping system according to claim 1, further comprising a means to vary the pump output performance curve.

6. The pumping system defined in claim 5, wherein the impeller comprises a plurality of flat blades.

7. The pumping system according to claim 5, the means to vary pump output performance curve comprises a digital computer executing an algorithm that controls the set point according to measurement of pump input rpm, motor current, motor power, or a combination thereof.

8. The pumping system according to claim 1, wherein the flow limiting characteristics includes at least the impeller which is configured to provide a performance curve slope and a pressure differential/flow such that a flow of fluid through the pump is maintained within defined limits over a wide applied pressure differential.

9. The pumping system according to claim 8, wherein said impeller includes a plurality of main blades and a plurality of splitter blades, shorter in length than the main blades, disposed between the main blades.

10. A system for pumping blood comprising:
    a) a rotodynamic pump including:
       i) a housing defining a chamber and an inlet and outlet in fluid communication with the chamber; and
       ii) an impeller disposed within the chamber for urging fluid from the inlet toward the outlet;
       iii) the pump having a performance curve at a nominal operating speed of the pump relating changes in the pressure differential across the pump to changes in flow through the pump, wherein the performance curve of the pump exhibits a change in flow of no more than 1 liter-per-minute for a change in pressure of 50 mm-Hg between the pump inlet and pump outlet;
    b) a driver for imparting rotational motion to the impeller
    c) a power supply for supplying power to the driver;
    d) a regulator for regulating the power supplied from the power supply to the driver;
    e) flow limiting characteristics that maintain the flow through the pump within predefined limits throughout a wide range of pressure differentials across the pump;
    f) means to vary the pump output performance curve, wherein the means to vary the pump output performance curve comprises a digital computer executing an algorithm that controls a set point according to measurement of pump input rpm, motor current, motor power, or a combination thereof; and
    wherein the pump further comprises an axial extension connected to the housing having a conical tip and wherein the impeller comprises a plurality of blades configured to accommodate the conical tip.

11. The pumping system according to claim 10, wherein the direction of flow through the impeller blades is at an acute angle with respect to the axis of rotation of the impeller.

12. The pumping system according to claim 10, wherein each blade of the plurality of blades is generally flat and includes a curved outer edge and an angled inner edge.

13. The pumping system according to claim 10, wherein the flow limiting characteristics includes at least the impeller which is configured to provide a performance curve slope and a pressure differential/flow pump such that a flow of fluid through the pump is maintained within defined limits over a wide applied pressure differential.

14. The pumping system according to claim 13, wherein said plurality of blades of the impeller includes a plurality of main blades and a plurality of splitter blades, shorter in length than the main blades, and disposed between the main blades.

* * * * *